US00PP27607P2

(12) United States Plant Patent
Hansen

(10) Patent No.: US PP27,607 P2
(45) Date of Patent: Jan. 24, 2017

(54) ***DIGITALIS* HYBRID PLANT NAMED 'BERRY CANARY'**

(50) Latin Name: *Digitalis×valinii*
Varietal Denomination: Berry Canary

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 121 days.

(21) Appl. No.: 14/544,458

(22) Filed: Jan. 8, 2015

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP25,442 P2 * 4/2015 Valin ..... Plt./263.1
PP25,640 P2 * 6/2015 Van der Sar ..... Plt./263.1

OTHER PUBLICATIONS

James Greenhouses 2014-2015 catalog, retrieved on Jun. 22, 2016, retrieved from the Internet at <http://www.jamesgreenhouses.com/pdfs/JG_Catalog_2014-15.pdf> 2 cover pages, pp. 1-7 and 35-38.*
Rice. Foxgloves for American Gardens. The American Gardener Mar./Apr. 2014, retrieved on Jun. 22, 2016, retrieved from the Internet at <http://mydigimag.rrd.com/publication/index.php?i=200971&m=&l=&p=33&pre=> pp. 29-33.*
The Commercial Greenhouse Grower Aug. 2015, retrieved on Jun. 23, 2016, retrieved from the Internet at <http://greenhousegrower.co.uk/wp-content/uploads/magazines/magazine-august-2015/files/assets/common/downloads/GHG%20August%202015.pdf> cover page and p. 8.*
Trademarks Electronic Search System, Digiplexis retrieved on Jun. 22, 2016, retrieved from the Internet at <http://tmsearch.uspto.gov/bin/showfield?f=doc&state=4802:29ejtj.2.1> 2 pp.*
Armitage. A new Digitalis hybrid. Plantsman (2015), vol. 14, No. 2 pp. 86-89.*

* cited by examiner

*Primary Examiner* — June Hwu

(57) ABSTRACT

The new and distinct cultivar of *Digitalis* interspecific hybrid plant named 'Berry Canary' is characterized by sturdy, upright and dense habit with dark-green, mostly-basal, serrate foliage and many-branched, large-flowered, open-faced, campanulate, self-cleaning, purplish rose flowers with light yellow throats and burgundy spotting over a long period. The flowers produce an abundance of nectar and are attractive to hummingbirds in the landscape.

1 Drawing Sheet

Botanical designation: *Digitalis×valinii.*
Cultivar denomination: 'Berry Canary'.

BACKGROUND OF THE INVENTION

The present invention relates to a new and distinct cultivar of hybrid plant, botanically known as *Digitalis×valinii*. The new *Digitalis×valinii* 'Berry Canary' is the product of a planned natural line breeding program conducted by Hans A. Hansen at a wholesale perennial nursery in Zeeland, Mich., USA. The objective of the breeding program was to create novel interspecific hybrid cultivars between *Digitalis purpurea* and *Digitalis canariensis* with excellent flowers, foliage and habit.

The new interspecific *Digitalis*×hybrid was a planned cross between a proprietary selection of purple spotted *Digitalis purpurea* 'Foxy' (not patented) as the female or seed parent times a proprietary selection of *Digitalis canariensis* (not patented) as the male or pollen parent in late winter of 2012 and later assigned the breeder code of H12-03-03. After further evaluation 'Berry Canary' was selected as a single plant from among several hundred crosses between various forms of such *Digitalis* hybrids and first asexually propagated by shoot tip cuttings in the summer of 2013 at the same wholesale perennial nursery in Zeeland, Mich. The new plant has since also been successfully asexually propagated by sterile shoot tip tissue culture. All of the resultant asexually propagated plants by cuttings and tissue culture have remained stable and reproduced true to type in successive generations.

SUMMARY OF THE INVENTION

Plants of the foxglove plant cultivar *Digitalis* 'Berry Canary' have not been observed under all possible environmental conditions. The phenotype may vary somewhat with variations in environment such as fertilizer, temperature, light intensity and photoperiod and plant growth regulators without, however, any variance in genotype.

The following traits in combination with one another have been repeatedly observed and are determined to be the unique characteristics of 'Berry Canary':

1. Sturdy, upright and dense growth habit.
2. High number of stiff basal branches extending bloom season from early summer till frost.
3. Large, open-faced, campanulate-formed, horizontal-facing, long-blooming, self-cleaning, non-secund flowers of purplish rose with light yellow throats with burgundy speckling.
4. Dark-green, sparsely-pubescent, mostly-basal, serrate leaves.

Plants of the new *Digitalis* can be compared to the female parent, *Digitalis purpurea* 'Foxy' in that the new plant has flowers that are larger, more pinkish coloring with smaller burgundy spotting, longer blooming season, more basal branching and taller habit. Compared to the male parent, *Digitalis canariensis*, with its yellowish orange flowers, the new plant has shorter habit and smaller foliage, pinkish purple with yellow flower coloration with spotting and is more winter hardy. The new plant is also more herbaceous producing more basal rosettes than the male parent which is more shrub-like. Compared to *Digitalis* 'Spice Island' U.S. Plant Pat. No. 17,849, the new plant develops into a taller plant, has a longer blooming season with more basal branching and pinkish purple flowers with yellow throats. Compared to *Digitalis* 'WALDIGONE' U.S. Plant Pat. No. 20,937, the new plant has less orange coloration in the flowers, is taller with more flowers and more basal branches. Compared to *Digitalis* 'Wedding Bells' U.S. Plant Pat. No. 22,578, the new plant is taller with more basal branching and longer flowering season and has flowers of more pinkish purple with yellow throat and burgundy spotting rather than white with khaki spotting. The foliage of 'Wedding Bells' is also more tomentose with silvery coloring rather than the sparsely pubescent and dark green color of 'Berry Canary'.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plants used in the drawings are second year growing plants following a vernalization period of about 8 weeks, grown in a greenhouse at a wholesale nursery in Zeeland, Mich. with supplemental fertilizer but without plant growth regulators.

DETAILED BOTANICAL DESCRIPTION

Figure 1:
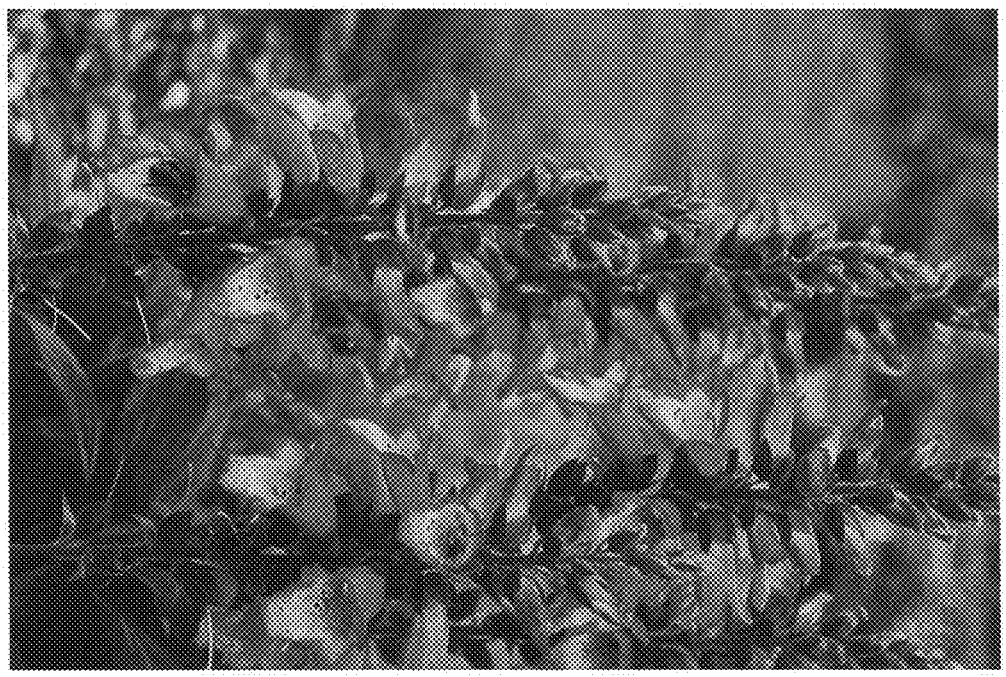
FIG. 1 shows a close-up of the flowers on the scape.
Figure 2:
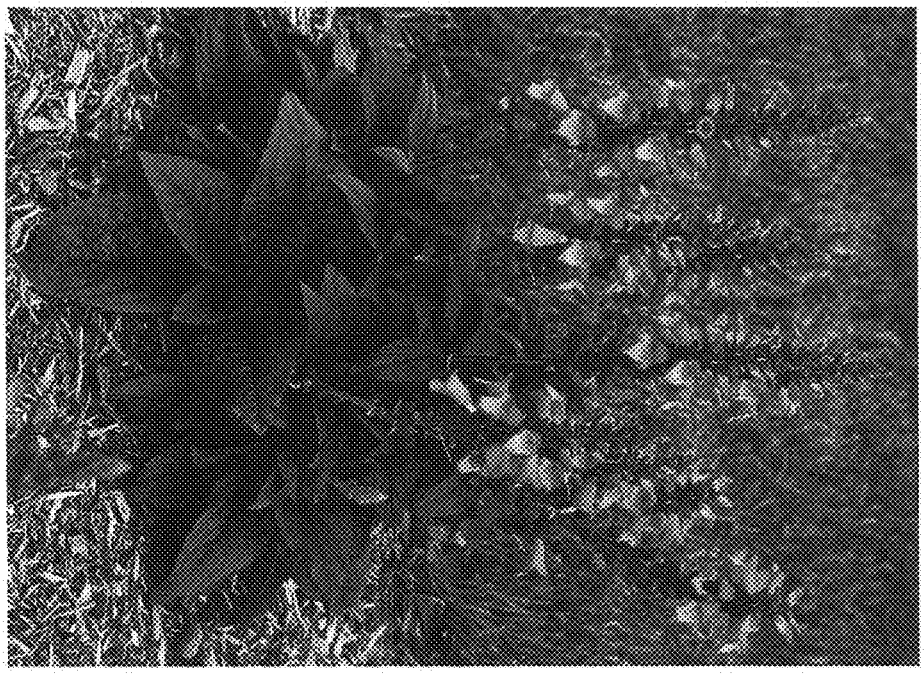
FIG. 2 shows the plant short, dense, rounded habit of a three year-old plant.

The following descriptions and color references are based on the 2001 edition of The Royal Horticultural Society Colour Chart except where common dictionary terms are used. The new plant, *Digitalis×valinii* 'Berry Canary', has not been observed under all possible environments. The phenotype may vary slightly with different environmental conditions, such as temperature, light, fertility, moisture and maturity levels, but without any change in the genotype. The following observations and size descriptions are of one-year-old plants in the loamy-sand open field trials of a nursery in Zeeland, Mich. with supplemental fertilizer and water as needed. The plants are natural habit and were not treated with plant growth regulators, nor were they pinched at any time in the growth year.

Parentage: Female, or seed parent an unnamed and unreleased selection of *Digitalis purpurea* 'Foxy'; male, or pollen parent unnamed, unreleased selection of *Digitalis canariensis*.

Propagation:

*Method.*—Shoot tip cuttings and sterile shoot tip plant tissue culture division.

Root description: Fine, freely branching; color creamy white near RHS 15D.

Time to initiate roots from tissue culture: About two weeks.

Crop time: Under normal cool spring growing conditions of 12° to 15° C., finished flowering plants can be obtained in about 8 to 10 weeks from a vernalized 25 mm plug.

Plant vigor: Very good.

Plant habit: Perennial, hardy from at least USDA zone 8 through 10 but capable of growing in colder regions as an annual; upright and dense; leaves cauline and dextrorse; tightly arranged, nodes about 5.0 mm apart in lower stem and 2.5 cm in upper portion before flowers, average about 8.0 mm apart; size with flowers about 120.0 cm tall and 55.0 cm across at widest point with branches.

Main stem: Stiff and erect; about 120.0 cm long and 2.5 cm diameter at base; lightly pubescent; cylindrical with ridges extended from central leaf veins; length of ridges extends to next lower leaf directly below; with basal branches and axillary branches.

Main stem color: More yellow than RHS 138D and lighter than RHS 146D with tinting nearest RHS 187B in regions of strong light exposure.

Basal stem: Curving upright next to main stem; about 65 cm long and 1.0 cm diameter; lightly pubescent; about two per plant; color and tinting same as main stem.

Axillary (secondary) branches: About 20 per plant; curving upward to nearly erect; about 40 cm long and 6.0 mm diameter at base; lightly pubescent; flowering from secondary branches arising from nodes just below lowest flowers and continuing lower at each node; also forming tertiary branches in nodes below flowers; color and tinting same as main stem.

Tertiary branches: About 10.0 cm long and 3.0 mm diameter; secondary and tertiary branches lengthen if primary stem is removed soon after flowering; color same as other stems.

Foliage: Cauline and dextrorse; sessile; to about 24.0 cm long at base and 10.0 cm wide at widest point, average about 22.0 cm long and 8.5 cm; about 56 leaves per plant below initial flowers.

Leaf blade: Cuneate, with acute apex and attenuate to sessile base; very lightly pubescent on both surfaces; serrate to serrulate in distal region; lustrous above and slightly lustrous below.

Leaf blade color: Adaxial nearest RHS 139A, abaxial between RHS 138A and RHS 138B.

Veins: Pinnate; very lightly pubescent; ridged on bottom and slightly impressed above.

Vein color: Adaxial midrib and secondary veins near midrib between RHS 197B and RHS 197A, adaxial perimeter veins between RHS 139A and RHS 139B; abaxial midrib nearest RHS 145C with slight tinting of nearest RHS 185C toward base, secondary veins and perimeter veins nearest RHS 143C.

Flower: Campanulate with basal 3.5 cm of corolla tube fused, total corolla average size 4.5 cm long and face opening to 2.4 cm across; zygomorphic; with four main lobes, two side lobes smallest and nearly perpendicular to upper and lower lobes, lowest lobe longest and upper lobe widest; two side lobes about 1.2 cm wide at fusion and 4.0 cm long with broadly acute apex; upper lobe about 2.2 cm wide at fusion and 4.5 cm long with rounded apex; lowest lobe about 2.0 cm wide at fusion and 4.5 cm long; length of side lobes from fusion to apex about 1.2 cm, top lobe length about 1.3 cm and lowest lobe length about 1.6 cm; speckling or flecking on the lower half of the petal adaxial surfaces, concentrated on lowest lobe but extending up about half way the side lobes; adaxial speckling sizes vary from about 1.0 mm to less than 0.1 mm diameter and positioning random, sometimes extending to apex and near the base of the throat; abaxial speckling typically more concentrated and larger on lower and distil portions of lower petals and on smaller range on distal side lobes and upper abaxial petals; lowest lobe lightly pubescent on adaxial surfaces and puberulent on adaxial surface and margin; other lobes glabrous on abaxial and adaxial surfaces and puberulent on margins; top petal slightly carinate in middle portion of center; not persistent, self-cleaning; produces large amount of nectar.

Flower number: About 120 per main stem, about 68 per lateral branch and about 35 per axillary branch.

Flower color: Variable with maturity.

*Just after opening of lower lobe*.—Distal abaxial and adaxial one-third side and upper lobes between RHS 71A and RHS N77B with the speckling on lower lobe nearest RHS N77A, proximal two two-thirds of corolla abaxial surface nearest RHS 145C and proximal two-thirds of corolla adaxial surface between RHS 145C and RHS 145D.

*Just prior to pollen dehiscence*.—Distal 3.5 cm of abaxial upper and side lobespetals more purple than RHS 71B and more red than RHS N77B and gradually lightening to between lighter than RHS 71D and RHS 70C in lower lobe with speckles closer to RHS N77B than RHS N77A, and basal abaxial 1.0 cm between RHS 4D and RHS 1D of entire fused corolla tube, lower lobe adaxial distal 3 to 4 mm between RHS 71A and RHS 71B with proximal region nearest RHS 1D and speckles nearest RHS N77B.

*After pollen dehiscence and before flower abscission*.—Distal 3.5 cm of upper and side lobes abaxial surface nearest RHS 70B and gradually lightening to between RHS 71D and RHS 70C on abaxial surface of lower lobe, proximal 1.0 cm of entire corolla tube nearest RHS 11D, adaxial distal 4 to 5 mm nearest RHS 71A, central adaxial entire corolla tube 1.5 cm nearest RHS 155D, proximal 5 mm entire corolla tube portion nearest RHS 1C and 1.0 to 2.0 mm section outside the proximal portion between RHS 64B and RHS 186B with irregular dots of nearest RHS 158B surrounding speckles of RHS N77A on lower and side lobes adaxial surface.

Inflorescence: Average size 52.0 cm long and 18 cm wide with side branches.

Flower bract: Deltoid; acute to sharply acute apex and truncate sessile base; about 2.5 cm long and 1.3 cm across, decreasing distally.

Flower bract color: Both abaxial and adaxial nearest RHS 146B with slight apical tinting of nearest RHS 187A.

Natural flowering season: Early summer through frost.

Flower longevity: Individual flowers on plant lasting about 7 to 10 days; main flower spike stays in flower for at least three months under ideal conditions.

Fragrance: None detected.

Flower buds while lower lobe still curled upward: Tubular; about 3.0 cm long, 1.4 mm across and 8.0 mm tall; puberulent margin, outer surface glabrous.

Flower bud color: Basal portion nearest RHS 150C with distal portion around perimeter of petals nearest RHS 71A.

Sepals: Five, in two sets, two inner and three outer; persistent; acute apex, truncate base, entire and puberulent margin; puberulent abaxial and adaxial; about 1.8 cm long and 1.0 cm across at middle.

Sepal color: Adaxial and abaxial surfaces nearest RHS 137B.

Peduncle: Strong, erect; puberulent; about 75 cm long and 12.0 mm in diameter below first flowers; color nearest RHS 138B with variable tinting of nearest RHS N186C.

Pedicel: Puberulent; cylindrical; erect to 45 degree angle at flower anthesis; to 1.7 cm long and 2.0 mm diameter; color nearest RHS 137B.

Gynoecium: One; puberulent.

*Style*.—About 2.5 cm long and gradually tapering to about 1.0 mm diameter; color nearest RHS 69C toward stigma and nearest RHS 145B toward ovary.

*Stigma*.—Split in last 1.0 mm and about 0.5 mm wide; each half with acute apex; color lighter than RHS 155D.

*Ovary*.—Superior; slightly flattened ovoid, apex tapering to meet style; about 10 mm long and 5.0 mm across at base and 2.0 mm thick; color between RHS 138B and RHS 138A.

Androecium: Four, didynamous, longitudinal; one set extending further; further extending set dehiscing first; adnate to petal.

*Filaments*.—Four; flattened and curved along inside of petal; about 2.3 and 2.6 cm long and 1.0 mm diameter at base; color nearest RHS 71B ageing to nearest RHS N163D.

*Anther*.—Divergent; angled at attachment; each half about 4.0 mm long and each half about 2.0 mm across; color prior to dehiscence between RHS 15A and RHS 15B with tiny nearly microscopic speckling of nearest RHS 71A; color post dehiscence nearest RHS 199A.

*Pollen*.—Abundant, dust-like; color nearest RHS 158D.

Fruit: Mature seed pods rarely produced; and viable seed production have not yet been observed.

Seed: Viable seed production has not yet been observed.

Disease and pest resistance or tolerance: 'Berry Canary' is not normally bothered by rodents or deer in the landscape. Disease or pest resistance beyond that typical of other *Digitalis* hybrids has not been noted. The new plant performs best in full sun to slight shade with good drainage and regular watering.

It is claimed:

1. A new and distinct cultivar of *Digitalis* hybrid plant named 'Berry Canary' as illustrated and described.

* * * * *